United States Patent [19]
Albert et al.

[11] Patent Number: 5,888,515
[45] Date of Patent: *Mar. 30, 1999

[54] RHUS DERMATITIS TREATMENT COMPOSITION AND METHOD

[75] Inventors: Brian M. Albert, Upper St. Clair Township, Allegheny County, Pa.; R. Richard Riso, Marco Island, Fla.

[73] Assignee: Albros, L.P., Pittsburgh, Pa.

[*] Notice: This patent issued on a continued prosecution application filed under 37 CFR 1.53(d), and is subject to the twenty year patent term provisions of 35 U.S.C. 154(a)(2).

[21] Appl. No.: 989,067

[22] Filed: Dec. 11, 1997

[51] Int. Cl.⁶ .......................... A61K 35/78; A61K 31/70; A61K 31/045; A61K 47/00
[52] U.S. Cl. .................. 424/195.1; 514/23; 514/729; 514/782; 424/642
[58] Field of Search ................ 424/195.1, 642; 514/23, 782, 729

[56] References Cited

U.S. PATENT DOCUMENTS

| | | | |
|---|---|---|---|
| 4,259,318 | 3/1981 | Duhe et al. | 424/94 |
| 4,428,965 | 1/1984 | Elsohly et al. | 424/311 |
| 4,663,151 | 5/1987 | Waali | 424/45 |
| 5,011,689 | 4/1991 | Misenko | 424/195 |
| 5,443,847 | 8/1995 | West | 424/639 |

OTHER PUBLICATIONS

Gibson, Melvin R. et al., "Activity of Jewelweed and its Enzymes in the Treatment of Rhus Dermatitis", *Journal of the American Pharmaceutical Association*, (1950), pp. 294–296.

Gisvold, Ole, "The Effect of Some Adsorbents, Precipitants and Oxidants upon the Resin of Rhus Toxicodendron", *Journal of the American Pharmaceutical Association*, (1958), pp. 17–18.

Tyler, V.E., *Folklore and Folk Medicines*, American Institute of the History of Pharmacy, Madison, Wisconsin, 1987, 4 pp.

Long, D. et al., Embase Abstract No. 97270822, *Amer. Journal of Contact Dermatitis*, 8/3, (1997), 1 page.

FDC Reports, The Rose Sheet, vol. 10, Issue 41, Oct. 9, 1989, 2 pages.

*Primary Examiner*—Raymond Henley, III
*Attorney, Agent, or Firm*—Webb Ziesenheim Bruening Logsdon Orkin & Hanson, P.C.

[57] ABSTRACT

A poison ivy (and related dermatitis) treatment composition and method in which a novel composition containing a combination of active ingredients gives new and unexpected results over compositions of the prior art. The inventive composition includes three essential ingredients: extract (fresh sap) of jewelweed (Impatiens species); fresh sap of plantain leaf; and an aqueous colloidal dispersion of subdivided whole oat grains. It is believed that the amphiphilic nature of the aqueous colloidal oat dispersion both preserves the activity of the plantain and jewelweed enzymes, as a result of its oat oil fraction, and also enhances topical delivery to the epidermis due to its aqueous fraction and the stabilizing effect of the oat bran as bulking agent. At the same time the aqueous oat colloid dispersion provides an essential excipient and delivery agent for the jewelweed and plantain enzymes, it itself provides essential anti-inflammatory and antipruritic effect to minimize dermatitis exacerbation due to itching and scratching. In addition, the joint presence of the plantain and jewelweed saps is believed to give an enhanced anti-inflammatory effect as compared to the use of either plant sap alone.

12 Claims, No Drawings

RHUS DERMATITIS TREATMENT COMPOSITION AND METHOD

FIELD OF THE INVENTION

The present invention relates to a novel composition for treating poison ivy (*Rhus dermatitis*) and topical treatment methods using the novel composition.

BACKGROUND OF THE INVENTION

The present invention relates to a novel composition for the treatment of *Rhus dermatitis* associated with exposure to the irritant urushiol oil and other irritating constituents of the sap of the stems, leaves and roots of poison ivy, poison oak, poison sumac and related plants and plant parts. Urushiol oil itself can contain for example 3-alkylcatechols and 3-alkenylcatechols in which the alkyl or alkenyl moieties are generally 15–17 carbons in length, and compounds such as these can be extremely irritating to the skin.

Exposure to urushiol oils can occur in various ways, and the oils are generally exuded to a greater degree by the stems, leaves and roots to the extent that these plant parts are crushed, cut or otherwise disintegrated such as by fire. Downstream smoke from a fire involving urushiol oil-containing plants is a well known cause of severe poison-ivy type dermatitis, and the oils can be carried by boots, shoes, clothes, tools and equipment in ways that can transmit skin irritants even to those who did not come in contact with the originating plant parts. Even though oxidation neutralizes urushiol oils over time, and despite the variability in potency of plants such as these depending on their season of origin, in some cases urushiol oils carried on shoes or other transmission vectors can remain active for years. It is believed that at least fifty percent of the population of the United States is sensitive to the active agents in urushiol oils, and the inflammatory response they stimulate, when brought in contact with the skin, is notorious—and in many cases severe.

Various prior art patents and publications have addressed poison-ivy type dermatitis (*Rhus dermatitis*) and its treatment. U.S. Pat. No. 3,922,342 discloses the use of a hydrophilic ion exchange material to absorb, upon contact with exposed skin, the phenolic compounds in the urushiol oils to minimize subsequent dermatitis. U.S. Pat. No. 3,875,301 describes a process for treating poison ivy dermatitis with tetraalkyl diamines. U.S. Pat. No. 3,862,331 discloses treating poison oak or ivy with 2-butanone. U.S. Pat. No. 3,749,772 describes a skin coating composition made of film-forming acrylic polymer which forms a barrier against topical exposure to urushiol oils. U.S. Pat. No. 4,259,318 discloses a "poison ivy relief" composition containing p-diphenol oxidase. U.S. Pat. No. 4,389,418 discloses an emollient topical composition which commercially incorporates calamine for the treatment of poison ivy, insect bites, chicken pox rash and etc. U.S. Pat. No. 4,663,151 discloses an aluminum chlorhydrate composition for preventing and/or treating urushiol oil-associated dermatitis. U.S. Pat. No. 5,443,847, discussed further below, discloses detoxification of urushiol with manganese salts.

Naturally-occurring chemicals are also known for treating poison-ivy type dermatitis, see Gibson, M. R. et al., "Activity of Jewelweed and its Enzymes in the Treatment of *Rhus Dermatitis*," *Journal of the American Pharmaceutical Association*, pp. 294–296, Gisvold, "The Effect of Some Adsorbents, Precipitants and Oxidants upon the Resin of Rhus Toxicondendron," *Journal of the American Pharmaceutical Association*, pp. 17–18, and Scarborough, J., ed., *Folklore and Folk Medicines*, American Institute of the History of Pharmacy, Madison, Wis., 1987. These three articles all address the general applicability of jewelweed extract as an ameliorating agent for *Rhus dermatitis*, and the latter identifies the utility of plantain extract in this regard also. It should be noted that the Gibson et al. article calls into question the efficacy of jewelweed alone to ameliorate *Rhus dermatitis*, see page 295, column 2, last full paragraph, as does Scarborough, at the bottom of page 102. U.S. Pat. No. 5,011,689 discloses the use of crushed plants of the genus Plantago, preferably broadleaf Plantain, to form a salve for treating poison ivy. European Patent Application 88116810 discusses an *Impatiens capensis* (jewelweed) extract for use in treating poison ivy dermatitis.

In general, prior art methods and compositions have not provided a combination therapy in which urushiol oils are neutralized, skin layers are soothed, skin healing is promoted, and dermatitis pain and itching are minimized or eliminated, all from the application of a single specialized topical composition designed to accomplish all these goals. Specifically, poison ivy treatment methods and compositions heretofore have not adequately addressed the need to control inflammation and itching themselves as well as to neutralize the contact dermatitis active agent. As with all contact dermatitis, when the patient scratches the affected skin both the inflammation per se and the active agent exposure itself are exacerbated. A need thus remains for a composition which effectively neutralizes urushiol oils while simultaneously reducing the pain and itch adequately to prevent scratching or rubbing of the affected skin area.

SUMMARY OF THE INVENTION

In order to meet this need, the present invention is a *Rhus dermatitis* treatment composition and method in which a novel composition containing a combination of active ingredients gives new and unexpected results over compositions of the prior art. The inventive composition includes three essential ingredients: extract of jewelweed (Impatiens species such as *Impatiens capensis, Impatiens biflora, Impatiens balsamea*, and *Impatiens pallida*); extract of plantain leaf; and an aqueous colloidal dispersion of subdivided whole oat grains. In theory, without intending to be bound by this theory, the amphiphilic (i.e., simultaneously hydrophilic and lipophilic) nature of the aqueous colloidal oat dispersion both preserves the activity of the plantain and jewelweed enzymes, as a result of its oat oil fraction, and also enhances topical delivery to the epidermis due to its aqueous fraction and the stabilizing effect of cellulose and hemicellulose as bulking agents. At the same time that the aqueous oat colloid dispersion provides an essential excipient and delivery agent for the jewelweed and plantain enzymes, it itself provides essential anti-inflammatory and antipruritic effect to minimize dermatitis exacerbation by action of scratching. In addition, the joint presence of the plantain and jewelweed saps is believed to give an enhanced anti-inflammatory effect as compared to the use of either plant sap alone. Treatment of *Rhus dermatitis* with this composition may be prophylactic or ameliorative. In either case, the composition is applied topically, after which the treated area may be loosely covered or, preferably, is left exposed.

DETAILED DESCRIPTION OF THE INVENTION

The present invention is a composition intended for topical administration which neutralizes urushiol oils and promotes healing of *Rhus dermatitis* in an improved manner compared to prior art compositions. The inventive composition includes three essential ingredients: extract of jewelweed (Impatiens species such as *Impatiens capensis, Impatiens biflora, Impatiens balsamea*, and *impatiens pallida*); extract of plantain leaf; and an aqueous colloidal dispersion of subdivided whole oat grains. It is believed that the amphiphilic nature of the aqueous colloidal oat dispersion both preserves the activity of the plantain and jewelweed enzymes, as a result of its oat oil fraction, and also enhances topical delivery to the epidermis due to its aqueous fraction and the stabilizing effect of its cellulose and hemicellulose constituents as bulking agents. At the same time that the aqueous oat colloid dispersion provides an essential excipient and delivery agent for the jewelweed and plantain enzymes, it itself provides essential anti-inflammatory and antipruritic effect to minimize dermatitis exacerbation by action of scratching. In addition, the joint presence of the plantain and jewelweed saps is believed to give an enhanced anti-inflammatory effect as compared to the use of either plant sap alone.

In the context of the present invention, "extract" should be understood to constitute the fresh juice of the stems and/or leaves of the jewelweed or plantain plants, or the extract may in turn be derived from a solvent extraction method such as with propylene glycol or other aqueous solvent. The usual extraction method for fresh juice production is crushing and filtering, although any method for separating pure sap from the plants may be employed. Solvent extractions, with subsequent removal of the solvent from the plant extract if desired, may be performed by means known in the art. When the solvent extraction process is complete, the dilution factor for the plant extract should be noted and any compensations made. Amounts and ratios described below are for fresh jewelweed and plantain juice, or sap.

Treatment of *Rhus dermatitis* with the inventive composition may be prophylactic or ameliorative. In either case, the composition is applied topically, after which the treated area may be loosely covered or, preferably, is left uncovered.

Additional ingredients form part of the preferred embodiments of the inventive composition, because they enhance the combined characteristics attributable to the three key ingredients described above. These ingredients include: (1) chamomile extract, a known soothing topical herb extract; (2) submicronized zinc oxide as an anti-inflammatory agent; (3) manganese gluconate; (4) xanthan gum; (5) methyl paraben; (6) menthol; (7) benzalkonium chloride; (8) oil of geranium; and (9) topical anesthetic. The most preferred embodiment of the present invention thus includes twelve ingredients—the three key ingredients and all nine optional ones. Further explanation of certain of the optional ingredients appears below.

First, as to all twelve ingredients, it should be noted than none provides any substantial opacity to the inventive composition—not even the oat colloid. This is important as a cosmetic consideration because translucency in a topical composition provides consumer appeal. Even sufferers of *Rhus dermatitis* are reluctant to use old fashioned, opaque calamine lotions that can make lesions appear even worse than they are. The submicronized zinc oxide of the present invention is transparent within the present composition due to its extremely small particle size, and in the context of the present invention functions primarily as an anti-inflammatory agent, not a sunscreen. The oat colloid particles impart minimal opacity, but the composition as a whole is still translucent and really almost transparent.

Topical anesthetics as constituents of the present composition are optional due to the effective soothing action of the oat colloid. However, standard amounts of various topical anesthetics may be included in the present composition without departing from its essential nature, and these anesthetics may constitute novocaine, carbocaine, benzocaine, benzyl alcohol, lidocaine, pramoxine hydrochloride, or other known anesthetics suitable for topical application. Typical concentrations of anesthetic compounds, in the inventive composition, are generally on the order of about 0.1–5 percent by weight. The addition of menthol with or without anesthetic provides an anti-inflammatory and soothing effect similar to a pharmacologic anesthetic, primarily due to the cooling sensation it creates.

Manganese gluconate is a beneficial ingredient in certain embodiments of the present composition. Manganese is known to complex with the catechol constituents of urushiol oils, see U.S. Pat. No. 5,443,847 referenced above, but in its gluconate form it is especially compatible with the aqueous colloidal dispersion of oats because the gluconate fraction also tends to complex with the active moieties in urushiol oils. When xanthan gum is present it thickens the dispersion and increases the viscosity of the overall composition. Neither the gluconate nor the xanthan gum changes the amphiphilic character of the oat colloid itself.

It should be noted that, when present, oil of geranium is included as an anti-inflammatory agent and, only incidentally, serves as a fragrance to the composition. Methyl paraben and benzalkonium chloride, although well-known stabilizers and preservatives of topical dermatological and cosmetic compositions considered individually, are especially compatible with the inventive compositions when used together because they do not alter the amphiphilic character of the oat colloid excipient which is essential to the present invention.

Substitutions for methyl paraben may be made by means known in the art. For example, the commercial products Germaben II (0.5–1.0 percent) or Glydant Plus (0.1–0.3 percent) may either be used to replace the methyl paraben. Alternatively, 0.2 percent methyl paraben and 0.03 percent Kathon CG may be used in conjunction. In any case, the use of a small amount of a preservative in a composition such as that of the present invention is well within the skill of the art and in any case does not form a central feature of the disclosure herein.

The colloidal dispersion of whole oat grains which forms an important part of the inventive composition may be obtained by various methods known in the art. Oat grains may be subdivided or pulverized by any known means including grinding, milling, ultrasonic pulverization, etc., either before or after soaking in water. Preferably, oat grains are soaked in pure water prior to division and are kept in the same water during the dividing or milling process. The oil fraction of the colloidal dispersion of whole oat grains is therefore the same percentage as found in the oat grains themselves, subject to the diluting factor of the water in which the divided grains are dispersed. Preferably, the ratio of oat grains to water is about 30 percent in the aqueous colloidal dispersion of whole oat grains. In turn, the dispersion itself contains on a "dry" basis approximately 8.0 percent by weight oat oil, approximately 18.5 percent hydrolyzed proteins; and balance phytic acid, ferulic acid, and beta glucan(s), polysaccharides, celluloses including hemicellulose, minerals, vitamins, arabans, polyphenols, ash, fiber and ambient moisture (about 10 percent).

The ratios of incorporation of the various constituents discussed above are not as critical as the nature of the ingredients themselves, but the following provides general guidelines. Between 25–70 parts by weight jewelweed extract, between 15–45 parts by weight aqueous colloidal dispersion of oats and between 5–15 parts by weight plantain extract may be included in compositions according to the present invention. Preferably, the present composition includes about 50 parts by weight jewelweed sap, about 30 parts by weight aqueous colloidal oat dispersion, and about 10 parts by weight plantain sap, remainder optional ingredients (if any). Remaining ingredient amounts include, as general guidelines: about 2–4 parts by weight chamomile extract, preferably 3.45; 2–4 parts by weight submicronized zinc oxide, preferably 3.00; 1–3 parts by weight manganese gluconate, preferably 2.00; 0.5–1.5 parts by weight xanthan gum, preferably 1.00; 0.10–0.30 parts by weight methyl paraben, preferably 0.20; 0.1–5.0 parts by weight topical anesthetic, 0.1–0.2 parts by weight menthol, preferably 0.15; 0.01–0.10 parts by weight benzalkonium chloride, preferably 0.05; and 0.01–0.10 parts by weight oil of geranium, preferably 0.05.

The compositions according to the present invention are simple admixtures requiring no special techniques, temperatures, pressures or equipment to manufacture. As a general matter, the jewelweed and plantain saps and aqueous colloidal dispersion of oats are admixed first, after which any of the remaining optional ingredients are blended thoroughly into the initial admixture. Any mixing equipment known in the cosmetic formulation industry is suitable for preparation of the topical compositions of the present invention, and standard sterility techniques and laboratory practices should be followed. When feasible, the final admixture should be homogenized, although this is optional, prior to packaging of the product in tubes, jars, vials and applicator packaging known in the art.

It should be noted in particular that the fresh saps of both jewelweed and plantain leaf are known to have little if any storage stability. In this context, therefore, not only does the formulation of the present invention provide these active agents in effective combination but also provides a storage stable composition of pharmaceutical and commercial value.

Treatment of the skin with the present invention is straightforward and requires only application of an aliquot of the inventive composition to the skin, either manually or by means of an applicator.

The following example is illustrative.

EXAMPLE 1

One Hundred (100) g. of whole oat grains were soaked for forty-eight hours in 200 ml cold, pure water at room temperature. The soaked grains and water were pulverized in an ordinary kitchen blender to create an aqueous colloidal dispersion of whole oat grains; no fractions were removed. Thirty (30.00) parts by weight of the aqueous colloidal dispersion of oat grains were admixed with 50.00 parts by weight of fresh jewelweed sap and 10.00 parts by weight sap of fresh plantain leaf. After thorough admixture, the following items were blended in the order given: 3.45 parts by weight chamomile extract; 3.00 parts by weight submicronized zinc oxide; 2.00 parts by weight manganese gluconate; 1.00 part by weight xanthan gum; 0.20 parts by weight methyl paraben; 0.10 parts by weight pramoxine hydrochloride; 0.15 parts by weight menthol; 0.05 parts by weight benzalkonium chloride; and 0.05 parts by weight oil of geranium. Mixing was continued until a homogenous, thickened admixture formed, and the composition was manually loaded into small cosmetic dispenser tubes with narrow applicator tips.

Although the invention has been described with particularity above, with reference to particular methods, constituents and materials, the invention is only to be considered limited insofar as is set forth in the accompanying claims.

We claim:

1. A topical composition for the treatment of *Rhus dermatitis* comprising: jewelweed extract, plantain leaf extract, and a quantity of an aqueous colloidal dispersion of oat grains, in admixture.

2. The topical composition according to claim 1 wherein for 100 total parts by weight said jewelweed extract is present in the amount of about 25–70 parts by weight, wherein said plantain leaf extract is present in the amount of about 5–15 parts by weight, and wherein said aqueous colloidal dispersion of oat grains is present in the amount of about 15–45 parts by weight.

3. The topical composition according to claim 2 further comprising 50 parts by weight jewelweed extract, 30 parts by weight aqueous colloidal dispersion of oat grains, and 10 parts by weight plantain leaf extract.

4. The topical composition according to claim 3 wherein said jewelweed extract is derived from at least one of the species selected from the group consisting of *Impatiens capensis, Impatiens biflora, Impatiens balsamea*, and *Impatiens pallida*.

5. The topical composition according to claim 3 wherein an amount of at least one additional ingredient is present selected from the group consisting of chamomile extract, submicronized zinc oxide, manganese gluconate, xanthan gum, methyl paraben, menthol, benzalkonium chloride, oil of geranium, and topical anesthetic.

6. The topical composition according to claim 3 wherein at least two additional ingredients are present in the composition selected from the group consisting of chamomile extract, submicronized zinc oxide, manganese gluconate, xanthan gum, methyl paraben, menthol, benzalkonium chloride, oil of geranium, and topical anesthetic.

7. The topical composition according to claim 3 further containing a quantity of each of chamomile extract, submicronized zinc oxide, manganese gluconate, xanthan gum, methyl paraben, menthol, benzalkonium chloride, oil of geranium, and topical anesthetic.

8. The topical composition according to claim 3 further comprising about 2–4 parts by weight chamomile extract, 2–4 parts by weight submicronized zinc oxide, 1–3 parts by weight manganese gluconate, 0.5–1.5 parts by weight xanthan gum, 0.10–0.30 parts by weight methyl paraben, 0.05–0.15 parts by weight topical anesthetic, 0.1–0.2 parts by weight menthol, 0.01–0.10 parts by weight benzalkonium chloride, and 0.01–0.10 parts by weight of oil of geranium.

9. The topical composition according to claim 8 further comprising 3.45 parts by weight chamomile extract, 3.00 parts by weight submicronized zinc oxide, 2.00 parts by weight manganese gluconate, 1.00 part by weight xanthan gum, 0.20 parts by weight methyl paraben, 1.00 parts by weight topical anesthetic, 0.15 parts by weight menthol, 0.05 parts by weight benzalkonium chloride, and 0.05 parts by weight oil of geranium.

10. The topical composition according to claim 9 wherein said topical anesthetic is selected from the group consisting of novocaine, carbocaine, benzocaine, benzyl alcohol, lidocaine and pramoxine hydrochloride.

11. A method of treating skin to minimize *Rhus dermatitis* comprising topically applying a quantity of the composition according to claim 1 to an area of skin of an animal or human to be treated.

12. A method of treating skin to minimize *Rhus dermatitis* comprising topically applying a quantity of the composition according to claim 10 to an area of skin of an animal or human to be treated.

* * * * *